(12) United States Patent
Krause et al.

(10) Patent No.: US 9,666,181 B2
(45) Date of Patent: May 30, 2017

(54) SYSTEMS AND METHODS FOR TUNING AUTOMATIC SPEECH RECOGNITION SYSTEMS

(71) Applicants: University of Florida, Gainesville, FL (US); Cochlear Limited

(72) Inventors: Lee S. Krause, Indialantic, FL (US); Bonny Banerjee, Palm Bay, FL (US); Mark Skowronski, West Melbourne, FL (US); Rahul Shrivastav, Gainesville, FL (US); Alice E. Holmes, Gainesville, FL (US)

(73) Assignees: University of Florida Research Foundation, Inc., Gainesville, FL (US); Cochlear Limited, MacQuarie University (AU)

( * ) Notice: Subject to any disclaimer, the term of this patent is extended or adjusted under 35 U.S.C. 154(b) by 190 days.

(21) Appl. No.: 13/761,810

(22) Filed: Feb. 7, 2013

(65) Prior Publication Data

US 2013/0226574 A1 Aug. 29, 2013

Related U.S. Application Data

(63) Continuation of application No. 12/748,608, filed on Mar. 29, 2010, now abandoned, and a
(Continued)

(51) Int. Cl.
| | |
|---|---|
| *G10L 15/00* | (2013.01) |
| *G06G 7/48* | (2006.01) |
| *A61N 1/36* | (2006.01) |
| *G10L 15/06* | (2013.01) |
| *G10L 15/07* | (2013.01) |

(Continued)

(52) U.S. Cl.
CPC .......... *G10L 15/00* (2013.01); *A61N 1/36032* (2013.01); *G10L 13/00* (2013.01); *G10L 15/063* (2013.01); *G10L 15/07* (2013.01); *H04R 25/30* (2013.01); *G10L 2015/0631* (2013.01); *G10L 2015/0638* (2013.01); *H04R 25/505* (2013.01); *H04R 2225/43* (2013.01); *H04R 2225/67* (2013.01)

(58) Field of Classification Search
CPC .................................................... G10L 15/22
USPC ........................................................ 704/231
See application file for complete search history.

(56) References Cited

U.S. PATENT DOCUMENTS

| 4,817,156 A | * | 3/1989 | Bahl | ....................... G10L 15/14 |
|---|---|---|---|---|
| | | | | 704/244 |
| 4,953,112 A | * | 8/1990 | Widin | .................... H04R 25/70 |
| | | | | 600/559 |

(Continued)

*Primary Examiner* — David Hudspeth
*Assistant Examiner* — Timothy Nguyen
(74) *Attorney, Agent, or Firm* — Merchant & Gould P.C.

(57) ABSTRACT

A tuning system for tuning a speech recognition system includes a transmitter for sending a user response to a speech recognition system. The user response is based at least in part on a test stimulus that may be generated by the control system. A receiver receives a recognized response from the speech recognition system; this recognized response is based at least in part on the associated user response. An adjustment module adjusts at least one parameter of the speech recognition system based at least in part on at least one of the test stimulus, the associated user response, and the recognized response.

21 Claims, 12 Drawing Sheets

Related U.S. Application Data continuation-in-part of application No. 12/748,819, filed on Mar. 29, 2010, and a continuation-in-part of application No. 11/421,889, filed on Jun. 2, 2006, now abandoned, which is a continuation-in-part of application No. 10/872,313, filed on Jun. 18, 2004, now Pat. No. 7,206,416, application No. 13/761,810, which is a continuation-in-part of application No. 12/201,492, filed on Aug. 29, 2008, and a continuation-in-part of application No. 12/201,598, filed on Aug. 29, 2008.

(60) Provisional application No. 61/164,451, filed on Mar. 29, 2009, provisional application No. 61/164,450, filed on Mar. 29, 2009, provisional application No. 60/492,103, filed on Aug. 1, 2003.

(51) Int. Cl.
*H04R 25/00* (2006.01)
*G10L 13/00* (2006.01)

(56) References Cited

U.S. PATENT DOCUMENTS

| | | | | |
|---|---|---|---|---|
| 5,465,402 | A * | 11/1995 | Ono | H03J 1/005 455/161.2 |
| 6,036,496 | A * | 3/2000 | Miller | G09B 19/04 434/116 |
| 6,151,571 | A * | 11/2000 | Pertrushin | G10L 17/26 704/207 |
| 6,477,492 | B1 * | 11/2002 | Connor | G10L 25/69 379/1.02 |
| 6,851,048 | B2 * | 2/2005 | Armitage | H04R 25/70 381/314 |
| 7,006,971 | B1 * | 2/2006 | Stahl | G10L 15/08 704/242 |
| 7,206,416 | B2 * | 4/2007 | Krause | G10L 25/00 381/60 |
| 7,451,085 | B2 * | 11/2008 | Rose | G10L 15/08 704/244 |
| 2002/0183648 | A1 * | 12/2002 | Hou | H04M 1/2475 600/559 |
| 2002/0198712 | A1 * | 12/2002 | Hinde | G10L 15/06 704/251 |
| 2003/0036903 | A1 * | 2/2003 | Konopka | G10L 15/065 704/249 |
| 2003/0083591 | A1 * | 5/2003 | Edwards | A61B 5/121 600/559 |
| 2003/0104499 | A1 * | 6/2003 | Pressman | G01N 33/56966 435/7.23 |
| 2003/0190602 | A1 * | 10/2003 | Pressman et al. | 435/5 |
| 2003/0220796 | A1 * | 11/2003 | Aoyama | G10L 15/22 704/275 |
| 2003/0235156 | A1 * | 12/2003 | Gygi | G06F 11/2733 370/241 |
| 2004/0199393 | A1 * | 10/2004 | Arizmendi | G10L 15/285 704/277 |

* cited by examiner

| PARAMETER | DEFAULT | OPTIONS |
|---|---|---|
| STRATEGY | ACE | ACE, CIS, SPEAK |
| STIMULATION RATE | 750 Hz | 250 - 2400 Hz |
| PULSE WIDTH | 25μs | 25 - 400μs |
| NUMBER OF CHANNELS | 20 | < 22 |
| NUMBER OF MAXIMA | 8 | < 12 |
| FREQUENCY ALLOCATION | LOG-LINEAR FROM 250 - 10000 Hz | MULTIPLE OPTIONS |
| GAIN | FLAT | MULTIPLE OPTIONS |
| GLOBAL THRESHOLD AND COMFORT MODIFIERS | NONE | INCREMENTS OF 1 - 30% |
| Q-VALUE | 20 | < 30 |
| BASE LEVEL | 4 | 0-6 |
| JITTER | 0% | 20% |

FIG. 3A

CI MAPPING STRATEGY PARAMETERS

In general the following principals apply for the CI Device Speech Processing strategies:
- Spectral resolution (SPEAK)
  - Site of stimulation: channel selection
  - Large number of channels desirable
- Temporal resolution (CIS)
  - Amplitude pattern of stimulation at a site
  - High pulse rate on each channel desirable
- The ACE strategy is a combination of both spectral and temporal resolution Parameters that must be chosen prior to measurements of Thresholds and Comfort Values:
1. Stimulation Rate***
   a. For CIS: rate X number of Channels < 14,400 Hz
   b. For ACE and SPEAK: Rate X number of Maxima < 14,400 Hz
2. Pulse width (Default is 25μs; range is from 25 - 150μs)
*** for higher stimulation rates the Ts and Cs measured can be used for either an ACE or CIS map as long as the total stimulation rate does not exceed 14,400 Hz Parameters that can be changed once the Threshold and Comfort Values have been obtained:
1). Number of Channels (CIS) or number of maxima (SPEAK or ACE) as long as total stimulation rate does not exceed 14,400 Hz
2). Deactivation of selected channels
3). Frequency Allocation
4). Gain - either globally or for individual channels
5). Global T and C modifiers
6). Q-Value - global modifier that changes the slope digital input level to the stimulus level output - amplitude curve
7). Base Level - minimum input level that produces stimulation
   a. Decreasing: softer sounds are audible [increases the Input Dynamic Range (IDR) of the processor]
   b. Increasing: softer sounds are not processed
8). Jitter: % of random variation to pulse rate
9). Channel ordering - in very rare cases the cochlea does not follow the normal tonotopic organization of the normal auditory system

FIG. 3B

SYSTEMS AND METHODS FOR TUNING AUTOMATIC SPEECH RECOGNITION SYSTEMS

CROSS-REFERENCE TO RELATED APPLICATIONS

This application is a continuation of U.S. patent application Ser. No. 12/748,608, filed Mar. 29, 2010 (now abandoned), which claims the benefit of and priority to U.S. Provisional Patent Application No. 61/164,451, filed Mar. 29, 2009. Additionally, this application claims priority to and is a continuation-in-part of U.S. patent application Ser. No. 12/748,819, filed Mar. 29, 2010 (now U.S. Pat. No. 9,553,984), which is a continuation-in-part of U.S. patent application Ser. No. 11/421,889, filed Jun. 2, 2006 (now abandoned), which is a continuation-in-part of U.S. patent application Ser. No. 10/872,313, filed Jun. 18, 2004, now U.S. Pat. No. 7,206,416, which claims the benefit of U.S. Provisional Patent Application No. 60/492,103, filed Aug. 1, 2003. U.S. patent application Ser. No. 12/748,819 claims priority to U.S. Provisional Patent Application No. 61/164,450, filed Mar. 29, 2009. This application is a continuation-in-part of U.S. patent application Ser. No. 12/201,598, filed Aug. 29, 2008 (now U.S. Pat. No. 9,319,812). This application is a continuation-in-part of U.S. patent application Ser. No. 12/201,492, In addition, this application claims priority to U.S. patent application Ser. No. 12/201,598, filed Aug. 29, 2008 (now U.S. Pat. No. 9,319,812) and U.S. patent application Ser. No. 12/201,492, filed Aug. 29, 2008, the complete disclosures of all of which are incorporated by reference herein.

FIELD OF THE INVENTION

This invention relates generally to tuning automatic speech recognition systems, and more specifically, self-tuning automatic speech recognition systems based on a user's speech model.

BACKGROUND

Multi-channel Cochlear Implant (CI) systems consist of an external headset with a microphone and transmitter, a body-worn or ear-level speech processor with a battery supply, and an internal receiver and electrode array. The microphone detects sound information and sends it to the speech processor which encodes the sound information into a digital signal. This information then is sent to the headset so that the transmitter can send the electrical signal through the skin via radio frequency waves to the internal receiver located in the mastoid bone of an implant recipient.

The receiver sends the electrical impulses to the electrodes implanted in the cochlea, thus stimulating the auditory nerve such that the listener receives sound sensations. Multi-channel CI systems utilize a plurality of sensors or electrodes. Each sensor is associated with a corresponding channel which carries signals of a particular frequency range. Accordingly, the sensitivity or amount of gain perceived by a recipient can be altered for each channel independently of the others.

In recent years, CI systems have made significant strides in improving the quality of life for profoundly hard of hearing individuals. CI systems have progressed from providing a minimal level of tonal response to allowing individuals having the implant to recognize upwards of 80 percent of words in test situations. Much of this improvement has been based upon improvements in speech coding techniques. For example, the introduction of Advanced Combination Encoders (ACE), Continuous Interleaved Sampling (CIS) and HiResolution, have contributed to improved performance for CI systems, as well as other digital hearing enhancement systems which incorporate multi-channel and/or speech processing techniques.

Once a CI system is implanted in a user, or another type of digital hearing enhancement mechanism is worn by a user, a suitable speech coding strategy and mapping strategy must be selected to enhance the performance of the CI system for day-to-day operation. Mapping strategy refers to the adjustment of parameters corresponding to one or more independent channels of a multi-channel CI system or other hearing enhancement system. Selection of each of these strategies typically occurs over an introductory period of approximately six or seven weeks during which the hearing enhancement system is tuned. During this tuning period, users of such systems are asked to provide feedback on how they feel the device is performing. The tuning process, however, is not a user-specific process. Rather, the tuning process is geared to the average user.

More particularly, to create a mapping for a speech processor, an audiologist first determines the electrical dynamic range for each electrode or sensor used. The programming system delivers an electrical current through the CI system to each electrode in order to obtain the electrical threshold (T-level) and comfort or max level (C-level) measures defined by the device manufacturers. T-level, or minimum stimulation level, is the softest electrical current capable of producing an auditory sensation in the user 100 percent of the time. The C-level is the loudest level of signal to which a user can listen comfortably for a long period of time.

The speech processor then is programmed, or "mapped," using one of several encoding strategies so that the electrical current delivered to the implant will be within this measured dynamic range, between the T- and C-levels. After T- and C-levels are established and the mapping is created, the microphone is activated so that the patient is able to hear speech and sounds in the environment. From that point on, the tuning process continues as a traditional hearing test. Hearing enhancement device users are asked to listen to tones of differing frequencies and volumes. The gain of each channel further can be altered within the established threshold ranges such that the patient is able to hear various tones of differing volumes and frequencies reasonably well. Accordingly, current tuning practice focuses on allowing a user to become acclimated to the signal generated by the hearing device.

The above-mentioned tuning technique has been developed to meet the needs of the average user. This approach has gained favor because the amount of time and the number of potential variables involved in designing optimal maps for individual users would be too daunting a task. For example, additional complications to the tuning process exist when users attempt to add subjective input to the tuning of the hearing enhancement system. Using subjective input from a user can add greater complexity to the tuning process as each change in the mapping of a hearing enhancement system requires the user to adjust to a new signal. Accordingly, after a mapping change, users may believe that their ability to hear has been enhanced, while in actuality, the users have not adjusted to the new mapping. As users adjust to new mappings, the users' hearing may in fact have been degraded.

Tuning methods and systems also have value outside of the cochlear implant or hearing device space, for example, for speech recognition ("ASR") systems. ASR systems are often incorporated into such technologies as cellular or other phones (in so-called "voicedial" or "speak-to-talk" systems), computer-based speech-to-text software for word processing, voicemail-to-email conversion systems (that send the contents of an audio voicemail in a text email format), and automated phone systems (for example, automated call-in centers for customer service). A tuning system would allow an ASR system to be tuned to match a particular speech model of a user, notwithstanding the ASR system's initial programming, thus making the technology in which the ASR system is incorporated useful for a larger number of users.

Since different people pronounce the same words differently, it is helpful to tune an ASR system to a user's particular speech model. Such tuning allows ASR systems to be modified such that the system perceives an appropriate stimulus, notwithstanding any particular speech model of the person using the ASR system. Returning to the voicedial or speak-to-talk example, if the ASR system contained in the cell phone is initially set at the point of manufacture to recognize stimuli as spoken by a typical speaker, it should operate properly when such a typical speaker (i.e., one that suffers from no speech-related impediment) uses the ASR system. However, if that ASR system is being used by a person with a speech impediment, it may incorrectly recognize certain stimuli, and may dial the incorrect contact or take other inappropriate action.

What is needed is a tuning system that would allow an ASR system to be tuned to match the particular speech model of any user, notwithstanding its initial programming, thus making the device useful for a larger number of users. Research has been performed regarding such systems for tuning ASR systems, but the resulting tuning systems still display performance limitations.

SUMMARY OF THE INVENTION

The present invention, according to one embodiment, provides a solution for tuning hearing enhancement systems. The inventive arrangements disclosed herein can be used with a variety of digital hearing enhancement systems including, digital hearing aids and cochlear implant systems. Other exemplary systems in which the inventive arrangements disclosed herein can be used include mobile phones configured to communicate via a cellular communications network and/or wireless ad hoc network. Still another exemplary system is a telephone configured to communication via a Voice-over-Internet-Protocol (VoIP) network and/or adapted to communicate via a plain old telephone service (POTS) network. These various systems are herein referred to collectively as "hearing devices." In accordance with the present invention, rather than using conventional hearing tests where only tones are used for purposes of testing a hearing device, speech perceptual tests can be used.

More particularly, speech perceptual tests wherein various words and/or syllables of the test are representative of distinctive language and/or speech features can be correlated with adjustable parameters of a hearing device. By detecting words and/or syllables that are misrecognized by a user, the hearing device can be tuned to achieve improved performance over conventional methods of tuning hearing devices.

In other embodiments, the present invention provides a solution for characterizing various communications channels and adjusting those channels to overcome distortions and/or other deficiencies.

One aspect of the present invention can include a method of tuning a digital hearing device. The method can include playing portions of test audio, wherein each portion of test audio represents one or more distinctive features of speech, receiving user responses to played portions of test audio heard through the digital hearing device, and comparing the user responses with the portions of test audio. An operational parameter of the digital hearing device can be adjusted according to the comparing step, wherein the operational parameter is associated with one or more of the distinctive features of speech.

In another embodiment, the method can include, prior to the adjusting step, associating one or more of the distinctive features of the portions of test audio with the operational parameter of the digital hearing device. Each distinctive feature of speech can be associated with at least one frequency or temporal characteristic. Accordingly, the operational parameter can control processing of frequency and/or temporal characteristics associated with at least one of the distinctive features.

The method further can include determining that at least a portion of the digital hearing device is located in a sub-optimal location according to the comparing step. The steps described herein also can be performed for at least one different language as well as for a plurality of different users of similar hearing devices.

Another aspect of the present invention can include a method of evaluating a communication channel. The method can include playing, over the communication channel, portions of test audio, wherein each portion of test audio represents one or more distinctive features of speech. The method can include receiving user responses to played portions of test audio, comparing the user responses with the portions of test audio, and associating distinctive features of the portions of test audio with operational parameters of the communication channel.

In another embodiment, the method can include adjusting at least one of the operational parameters of the communication channel according to the comparing and associating steps. Notably, the communication channel can include an acoustic environment formed by an architectural structure, an underwater acoustic environment, or the communication channel can mimic aviation effects on speech and hearing. For example, the communication channel can mimic effects such as G-force, masks, and the Lombard effect on hearing. The steps disclosed herein also can be performed in cases where the user exhibits signs of stress or fatigue.

Other embodiments of the present invention can include a machine readable storage programmed to cause a machine to perform the steps disclosed herein as well as a system having means for performing the various steps described herein.

In another aspect, the invention relates to a tuning system for tuning a speech recognition system, the tuning system including a transmitter for sending an associated user response to a speech recognition system, wherein the associated user response is based at least in part on a test stimulus, a receiver for receiving a recognized response from a speech recognition system, wherein the recognized response is based at least in part on the associated user response, and an adjustment module for adjusting at least one parameter of a speech recognition system based at least in part on at least one of the test stimulus, the associated user response, and the recognized response. In an embodiment, the tuning system includes a test stimulus generation module for sending a test stimulus to a user. In another embodiment, the tuning system includes a comparison module for comparing the associated user response to the recognized response, wherein the comparison module identifies an error between the associated user response to the recognized response. In yet another embodiment, the tuning system includes a comparison module for comparing the test stimulus to the recognized response, wherein the comparison module identifies an error between the test stimulus to the recognized response. In still embodiment, the comparison module compares an acoustic feature of the test stimulus to an acoustic feature of the associated user response.

In another embodiment of the above aspect, the acoustic feature includes at least one of a cepstral coefficient and a speech feature. In another embodiment, the adjustment module adjusts the at least one parameter based at least in part on the error. In yet another embodiment, the adjustment module predicts at least a second parameter based at least in part on the error. In still another embodiment, the tuning system includes a storage module for storing at least one of the test stimulus, the associated user response, and the recognized response. In another embodiment, the storage module stores a plurality of test stimuli, a plurality of associated user responses, and a plurality of recognized responses. In another embodiment, the comparison module compares at least two of the plurality of test stimuli, the plurality of associated user responses, and the plurality of recognized responses and generates a speech model based at least on part on the comparison.

In another aspect, the invention relates to a method of tuning a speech recognition system, the method including the steps of transmitting an associated user response to a speech recognition system, wherein the associated user response is based at least in part on a test stimulus, receiving a recognized response from a speech recognition system, wherein the recognized response is based at least in part on the associated user response, and adjusting at least one parameter of a speech recognition system based at least in part on at least one of the test stimulus, the associated user response, and the recognized response. In an embodiment, the method includes selecting a test stimulus, and sending the test stimulus to a user. In another embodiment, the method includes the step of comparing the associated user response to the recognized response. In yet another embodiment, the method includes the step of storing the associated user response and the associated user response. In still another embodiment, the method includes the steps of repeating the selecting step, the sending step, the transmitting step, the receiving step, the adjusting step, the comparing step, and the storing step, and creating an error set.

In another embodiment of the above aspect, the error set includes a first difference between a first associated user response and a second recognized response and a second difference between a second associated user response and a second recognized response. In another embodiment, the method includes the step of predicting at least a second parameter based at least in part on the error set. In yet another embodiment, the comparing step compares an acoustic feature of the associated user response to an acoustic feature of the recognized response. In still another embodiment, the acoustic feature includes at least one of a cepstral coefficient and a speech feature.

In another aspect, the invention relates to an article of manufacture having computer-readable program portions embedded thereon for tuning a speech recognition system, the program portions including instructions for transmitting an associated user response to a speech recognition system, wherein the associated user response is based at least in part on a test stimulus, instructions for receiving a recognized response from a speech recognition system, wherein the recognized response is based at least in part on the associated user response, and instructions for adjusting at least one parameter of a speech recognition system based at least in part on at least one of the test stimulus, the associated user response, and the recognized response.

BRIEF DESCRIPTION OF THE DRAWINGS

There are shown in the drawings, embodiments which are presently preferred, it being understood, however, that the invention is not limited to the precise arrangements and instrumentalities shown.

FIGS. 3A and 3B are tables illustrating exemplary operational parameters of one variety of hearing enhancement system, such as a Cochlear Implant, that can be modified using suitable control software.

DETAILED DESCRIPTION OF THE INVENTION

Figure 1A:
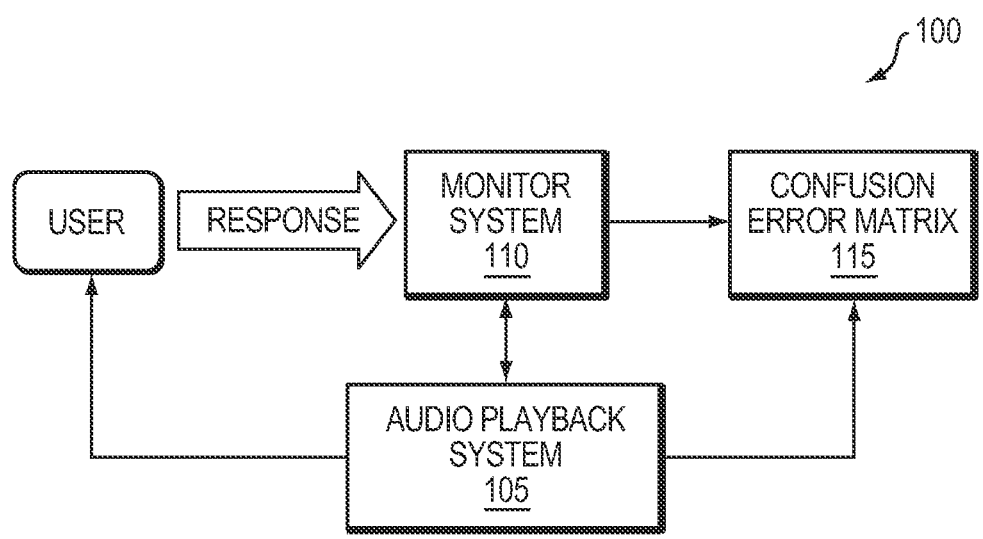
FIG. 1A is a schematic diagram illustrating an exemplary system for determining relationships between distinctive features of speech and adjustable parameters of a hearing enhancement system in accordance with the inventive arrangements disclosed herein.

FIG. 1A is a schematic diagram illustrating an exemplary system 100 for determining relationships between distinctive speech and/or language features and adjustable parameters of a hearing enhancement system (hearing device) in accordance with the inventive arrangements disclosed herein. As previously noted, such hearing devices can include any of a variety of digital hearing enhancement systems such as cochlear implant systems, digital hearing aids, or any other such device having digital processing and/or speech processing capabilities. Other hearing devices, in accordance with the invention, can include voice-based communication systems such as mobile phones configured to communicate via a cellular communications network and/or wireless ad hoc network, as well as telephones configured to communication via a Voice-over-Internet-Protocol (VoIP) network and/or adapted to communicate via a plain old telephone service (POTS) network.

More particularly, the system 100 can include an audio playback system (playback system) 105, a monitor 110, and a confusion error matrix (CEM) 115. The playback system 105 can audibly play recorded words and/or syllables to a user having a hearing device to be tuned. The playback system 105 can be any of a variety of analog and/or digital sound playback systems. According to one embodiment of the present invention, the playback system 105 can be a computer system having digitized audio stored therein. According to still another embodiment, the playback system 105 can include a text-to-speech (TTS) system capable of generating synthetic speech from input or stored text.

While the playback system 105 can simply play aloud to a user recorded and/or generated audio, it should be appreciated that in some cases the playback system 105 can be communicatively linked with the hearing device under test. For example, in the case of selected digital hearing aids and/or cochlear implant systems, an A/C input jack can be included in the hearing device that allows the playback system 105 to be connected to the hearing device to play audio directly through the A/C input jack without having to generate sound via acoustic transducers.

The playback system 105 can be configured to play any of a variety of different test words and/or syllables to the user (test audio). Accordingly, the playback system 105 can include or play commonly accepted test audio. For example, according to one embodiment of the present invention, the well-known Iowa Test Battery, as disclosed by Tyler et al. (1986), of consonant vowel, consonant nonsense words can be used. As noted, depending upon the playback system 105, a media such as a tape or compact disc can be played, the test battery can be loaded into a computer system for playback, or the playback system 105 can generate synthetic speech mimicking a test battery.

Regardless of the particular set or listing of words and/or syllables used, each of the words and/or syllables can represent a particular set of one or more distinctive features of speech. Two distinctive feature sets have been proposed. The first set of features, proposed by Chompsky and Halle (1968), is based upon the articulatory positions underlying the production of speech sounds.

Another set of features, proposed by Jakobson, Fant, and Halle (1963), is based upon the acoustic properties of various speech sounds. These properties describe a small set of contrastive acoustic properties that are perceptually relevant for the discrimination of pairs of speech sounds. More particularly, as will be readily understood by one of ordinary skill, the different distinctive features and their potential acoustic correlates can be broadly grouped into three categories: fundamental source features; secondary consonantal source features; and resonance features.

The fundamental source features can be further characterized on the basis of whether the speech sounds are vocalic or non-vocalic. Vocalic speech corresponds to speech sounds associated with vowels. Accordingly, such speech sounds correspond to a single periodic source, the onset of the speech not being abrupt; otherwise the speech sound can be characterized as non-vocalic. The fundamental source features also can be characterized on the basis of whether the speech sounds are consonantal or non-consonantal. Consonantal speech sounds correspond to sounds associated with consonants. Such speech sounds are characterized by the presence of zeros in the associated spectrum of the sounds.

The secondary consonantal source features can be further characterized on the basis of whether the speech sounds are interrupted or continuant. Continuant speech sounds, are also characterized as semi-vowels, because of their similar sound quality. There is little or no friction with continuant speech sounds as the air passes freely out through the mouth of the speaker. A continuant speech sound is produced with an incomplete closure of the vocal tract. Interrupted speech sounds, by contrast, end abruptly.

The secondary consonantal features can also be characterized on the basis of whether the speech sounds are checked or unchecked. Checked speech sounds, typified by some Far Eastern and African languages, are characterized by abrupt termination as opposed to gradual decay, whereas unchecked speech sounds are characterized by gradual decay. Additionally, secondary consonantal features can be characterized as strident or mellow. The former typically has an irregular waveform, whereas the latter typically has a smooth waveform. A secondary consonantal feature characterize as mellow also has a wider autocorrelation function relative to a corresponding normalized strident feature. Secondary consonantal features can also be classified according to whether the sound is voiced or voiceless.

The resonance features can be further characterized on the basis of whether the speech sound is compact or diffuse. A compact feature is associated with sound having a relative predominance of one centrally located format region, whereas a diffuse feature implies sound having one or more non-central formats. The resonance features can also be characterized as grave or acute. Speech sounds that are characterized as grave are low-frequency dominant low frequency, whereas those characterized as acute are high-frequency dominant. Additionally, resonance features can be characterized as flat or plain, depending on whether the there is a downward shift of some or all formats, typically associated with vowels and a reduction in lip orifice of the speaker.

The resonance features also can be further characterized as sharp or plain, the latter characterizing speech sounds whose second and/or higher formats rise. Moreover, resonance features can also be characterized as tense or lax, depending on the amount and duration of the energy of the sound. The resonance features also can be classified according to whether the speech sound is characterized as having a nasal format or a nasal murmur. The distinctive speech features and their potential acoustic correlates are further described in R. Jakobson, G. M. Fant, and M. Halle, PRELIMINARIES TO SPEECH ANALYSIS: THE DISTINCTIVE FEATURES AND THEIR CORRELATES (MIT Press, Cambridge; 1963), which is incorporated herein by reference in its entirety.

The above-described distinctive features of speech sounds and their potential acoustic correlates are only examples of the many different distinctive features of speech for which a relationship with one or more adjustable parameters can be determined according to the invention described herein. Accordingly, regardless of the particular distinctive features of speech of interest in a particular context the invention can determine relationships between the distinctive features and adjustable parameters for enhancing the capacity of a particular hearing device for a particular user of the device.

It should be appreciated that any of a variety of different features of speech can be used within the context of the present invention. Any feature set that can be correlated to test words and/or syllables can be used. As such, the invention is not limited to the use of a particular set of speech features and further can utilize a conglomeration of one or more feature sets.

The monitor system 110 can be a human being who records the various test words/syllables provided to the user and the user responses. In another embodiment, the monitor system 110 can be a speech recognition system configured to speech recognize, or convert to text, user responses. For example, after hearing a word and/or syllable, the user can repeat the perceived test audio aloud.

In yet another embodiment, the monitor system 110 can include a visual interface through which the user can interact. The monitor system can include a display upon which different selections are shown. Thus, the playback of particular test words or syllables can be coordinated and/or synchronized with the display of possible answer selections that can be chosen by the user. For example, if the playback system 105 played the word "Sam," possible selections could include the correct choice "Sam" and one or more incorrect choices, such as "sham." The user chooses the selection corresponding to the user's understanding or ability to perceive the test audio.

In any case, the monitor system 110 can note the user response and store the result in the CEM 115. The CEM 115 is a log of which words and/or syllables were played to the user and the user responses. The CEM 115 can store both textual representations of test audio and user responses and/or the audio itself, for example as recorded through a computer system or other audio recording system. As shown, the audio playback system 105 can be communicatively linked to the CEM 115 so that audio data played to the user can be recorded within the CEM 115.

While the various components of system 100 have been depicted as being separate or distinct components, it should be appreciated that various components can be combined or implemented using one or more individual machines or systems. For example, if a computer system is utilized as the playback system 105, the same computer system also can store the CEM 115. Similarly, if a speech recognition system is used, the computer system can include suitable audio circuitry and execute the appropriate speech recognition software.

Depending upon whether the monitor system 115 is a human being or a machine, the system 100, for example the computer, can be configured to automatically populate the confusion error matrix 115 as the testing proceeds. In that case, the computer system further can coordinate the operation of the monitor system 110, the playback system 105, and access to the CEM 115. Alternatively, a human monitor 110 can enter testing information into the CEM 115 manually.

Figure 1B:
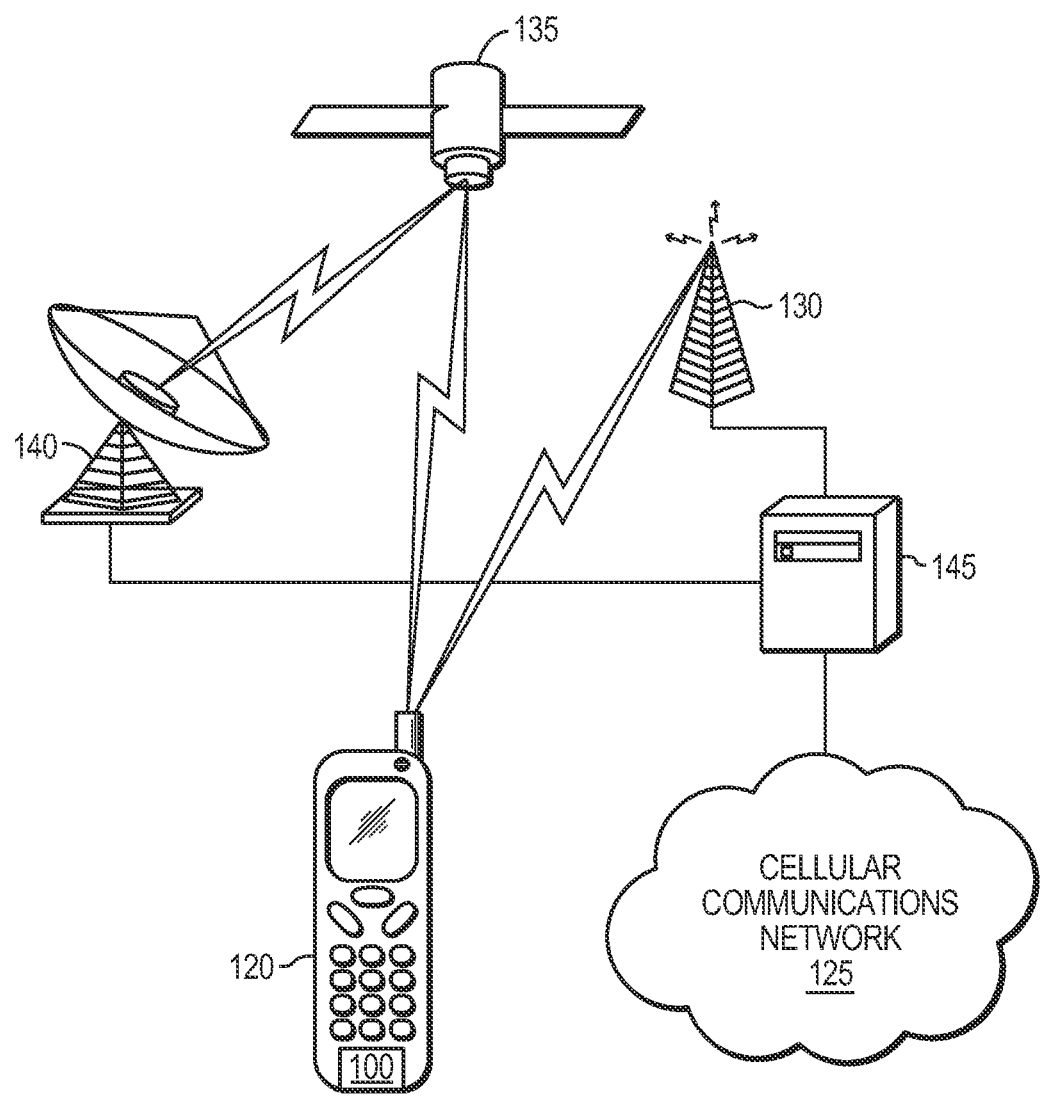
FIG. 1B is a schematic diagram of a cellular phone configured to communicate via a cellular communications network and including a system for determining relationships between distinctive features of speech and adjustable parameters in order to tune the cellular phone to the hearing requirements of a particular user in accordance with the inventive arrangements disclosed herein.

FIG. 1B is a schematic diagram of a communications environment in which the system 100, as described can be employed according one embodiment of the invention. The communications environment is a cellular communication environment in which the particular hearing device is cellular phone 120. The system 100 is illustratively integrated into the cellular phone 120. The cellular phone 120 can communicate via cellular communications network 125 with other communications devices (not shown) that also communicatively link to the cellular communications network. The cellular phone 120 illustratively conveys and receives wireless communications signals via a cellular tower 130 and/or a communications satellite 135, the latter also illustratively communicating via wireless signals to a ground station 140. Signals between the cellular tower 130 and ground station 140 are illustratively exchanged with a server 145 or other application-specific device, as will be readily understood by one of ordinary skill in the art.

In performing the functions described herein, the system 100 can be used to improve or optimize the cellular phone 120 so as to accommodate the unique hearing needs of a particular user of the device. Specifically, the system 100 allows the cellular phone to be programmed to present a series of speech sounds to a user of the cellular phone 120 in which the system is integrated. The user can repeat the sounds into the cellular phone 120. The system-presented sounds and the user's responses are compared using automatic speech recognition techniques based upon distinctive feature analysis, according to the invention. The difference—or errors—obtained using two sets of distinctive features can be used to tune the cellular phone 120; that is, the comparison and distinctive feature analysis applied by the system, provides a basis by which to adjust operation parameters of the device to accommodate the particular hearing needs of the user. Appropriate tuning can improve the intelligibility of the speech heard by the user of the cellular phone 120.

Figure 1C:
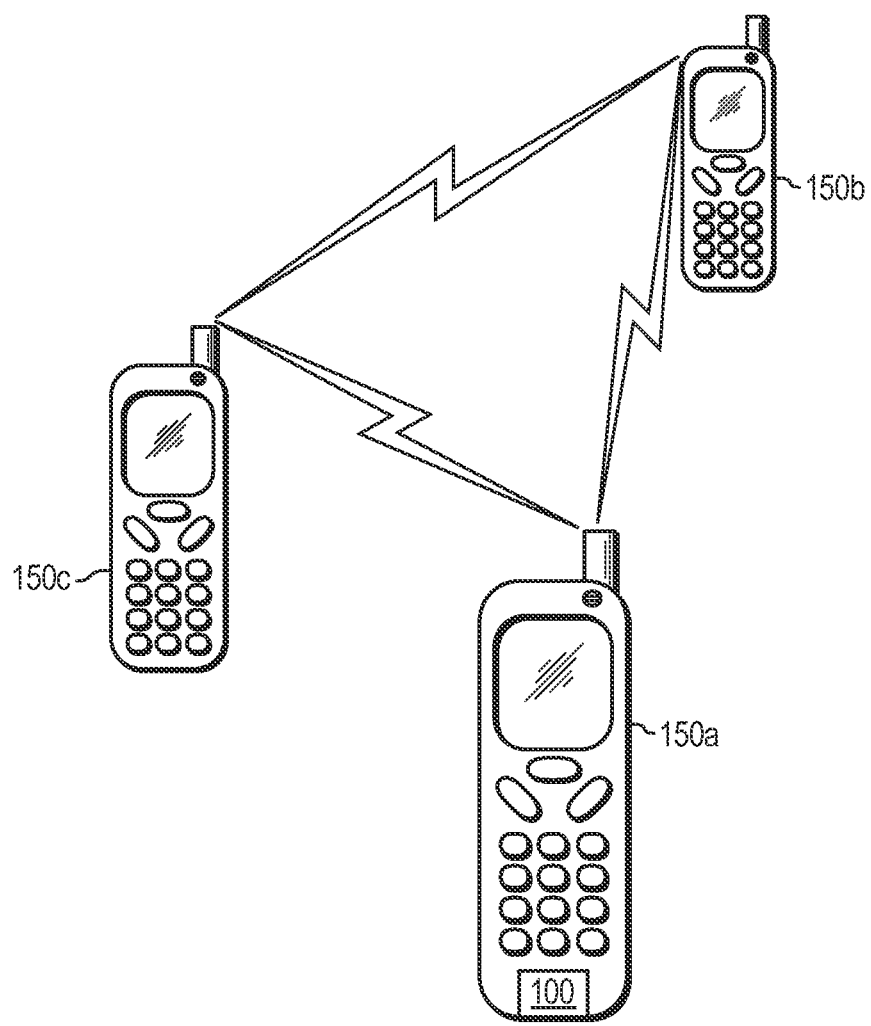
FIG. 1C is a schematic diagram of a mobile phone configured to communicate via a wireless ad hoc communications network and including a system for determining relationships between distinctive features of speech and adjustable parameters in order to tune the cellular phone to the hearing requirements of a particular user in accordance with the inventive arrangements disclosed herein.

FIG. 1C is a schematic diagram of an alternative communications environment in which the system 100, as described, can be employed according to yet another embodiment of the invention. The illustrated environment, according to this embodiment, comprises an ad hoc wireless network in which a plurality of wireless communications devices 150a-c communicate directly with one another through the exchange of wireless communications signals. At least one of the plurality of devices defines a hearing device 150a, which according to the present invention, includes the system 100 having the afore-described components of the system integrated into the device. Operatively, the system 100 presents sounds and compares the users response, comparing the differences and applying distinctive feature analysis, the system 100 tunes the mobile device 150a. Thus, again, the system 100 can be used to improve or optimize the mobile hearing device 150a so as to accommodate the specific hearing needs of the user.

Figure 1D:
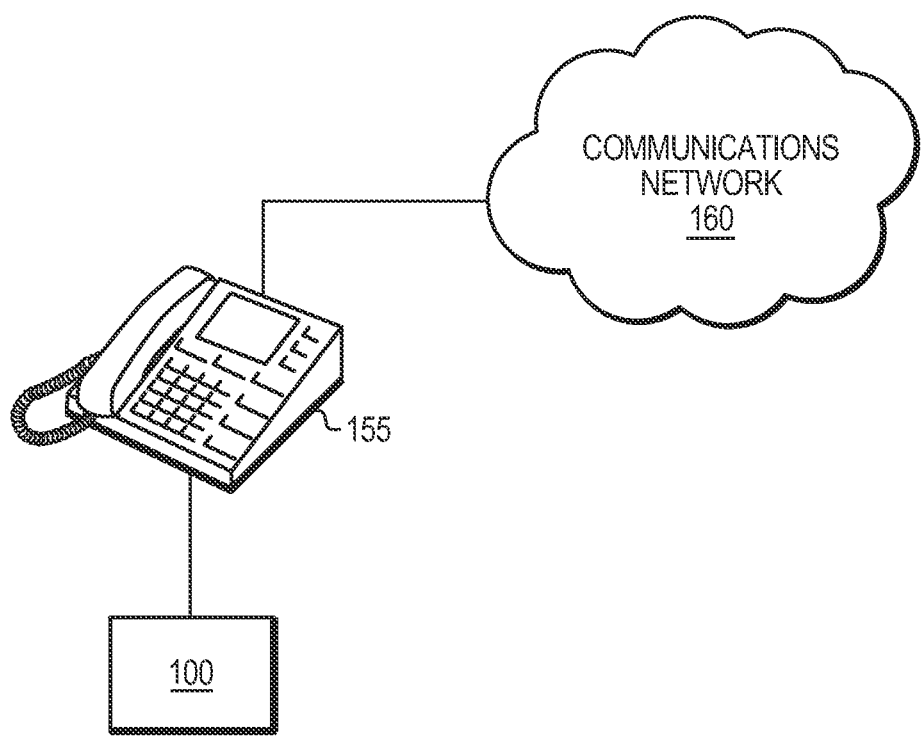
FIG. 1D is a schematic diagram of a telephone configured to communicate via a telephony communications network and including a system for determining relationships between distinctive features of speech and adjustable parameters in order to tune the telephone to the hearing requirements of a particular user in accordance with the inventive arrangements disclosed herein.

FIG. 1D is a schematic diagram of yet a different communications environment in which the system 100 can be employed according to still another embodiment of the invention. Within this environment, the hearing device is a telephone 155, such as a plain old telephone service (POTS) telephone or a VoIP telephone, configured to communicate with other devices (not shown) via a communications network 160 which comprises a POTS and/or data communications network. The system 100, whose components and operative features are those described herein, illustratively comprises a separate unit communicatively linked to the telephone 155. Alternatively, however, the system can be integrated into the telephone 155. Operatively, the system 100 presents to the user of the telephone 155 certain sounds.

Differences—or errors—between the device-presented sounds and the user's response to the sounds are compared. Applying distinctive feature analysis, as described herein, the system 100 tunes the telephone 155 so that the telephone is operatively configured to accommodate the particular hearing needs of the telephone user.

Figure 2:
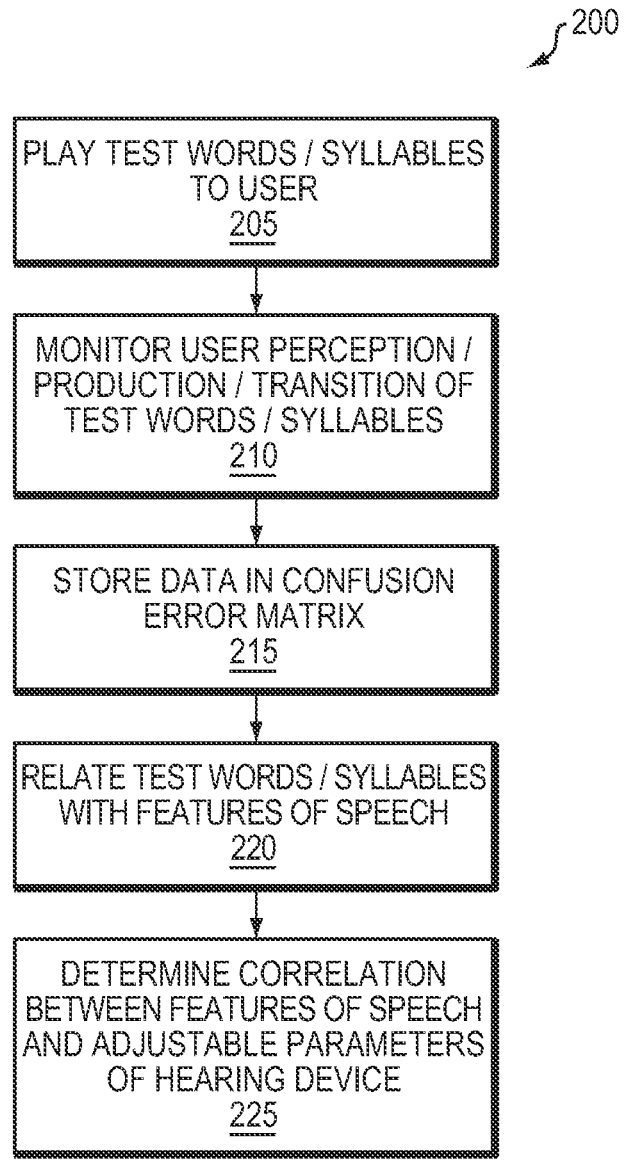
FIG. 2 is a flow chart illustrating a method of determining relationships between distinctive features of speech and adjustable parameters of hearing enhancement systems in accordance with the inventive arrangements disclosed herein.

FIG. 2 is a flow chart illustrating a method 200 of determining relationships between features of speech and adjustable parameters of hearing devices in accordance with the inventive arrangements disclosed herein. The method 200 can begin in a state where a hearing device worn by a user is to be tuned. In accordance with one aspect of the present invention, the user has already undergone an adjustment period of using the hearing device. For example, as the method 200 is directed to determining relationships between distinctive features of speech and parameters of a hearing device, it may be desirable to test a user who has already had ample time to physically adjust to wearing a hearing device.

The method 200 can begin in step 205 where a set of test words and/or syllables can be played to the user. In step 210, the user's understanding of the test audio can be monitored. That is, the user's perception of what is heard, production of what was heard, and transition can be monitored. For example, in one aspect of the present invention, the user can repeat any perceived audio aloud. As noted, the user responses can be automatically recognized by a speech recognition system or can be noted by a human monitor. In another aspect, the user can select an option from a visual interface indicating what the user perceived as the test audio.

In step 215, the test data can be recorded into the confusion error matrix. For example, the word played to the user can be stored in the CEM, whether as text, audio, and/or both. Similarly, the user responses can be stored as audio, textual representations of audio or speech recognized text, and/or both. Accordingly, the CEM can maintain a log of test words/syllables and matching user responses. It should be appreciated by those skilled in the art that the steps 205, 210 and 215 can be repeated for individual users such that portions of test audio can be played sequentially to a user until completion of a test.

After obtaining a suitable amount of test data, analysis can begin. In step 220, each error on the CEM can be analyzed in terms of a set of distinctive features represented by the test word or syllable. The various test words and/or syllables can be related or associated with the features of speech for which each such word and/or syllable is to test. Accordingly, a determination can be made as to whether the user was able to accurately perceive each of the distinctive features as indicated by the user's response. The present invention contemplates detecting both the user's perception of test audio as well as the user's speech production, for example in the case where the user responds by speaking back the test audio that is perceived. Mispronunciations by the user can serve as an indicator that one or more of the distinctive features represented by the mispronounced word or syllable are not being perceived correctly despite the use of the hearing device. Thus, either one or both methods can be used to determine the distinctive features that are perceived correctly and those that are not.

In step 225, correlations between features of speech and adjustable parameters of a hearing device can be determined. For example, such correlations can be determined through an empirical, iterative process where different parameters of hearing devices are altered in serial fashion to determine whether any improvements in the user's perception and/or production result. Accordingly, strategies for altering parameters of a hearing device can be formulated based upon the CEM determined from the user's test session or during the test session.

In illustration, studies have shown that with respect to the distinctive features referred to as grave sounds, such sounds are characterized by a predominance of energy in the low frequency range of speech. Acute sounds, on the other hand, are characterized by energy in the high frequency range of speech. Accordingly, test words and/or syllables representing grave or acute sounds can be labeled as such. When a word exhibiting a grave or acute feature is misrecognized by a user, the parameters of the hearing device that affect the capability of the hearing device to accurately portray high or low frequencies of speech, as the case may be, can be altered. Thus, such parameters can be associated with the misrecognition of acute and/or grave features by a user. Similarly, interrupted sounds are those that have a sudden onset, whereas continuant sounds have a more gradual onset. Users who are not able to adequately discriminate this contrast may benefit from adjustments to device settings that enhance such a contrast.

According to one embodiment of the present invention, Modeling Field Theory (MFT) can be used to determine relationships between operational parameters of hearing devices and the recognition and/or production of distinctive features. MFT has the ability to handle combinatorial complexity issues that exist in the hearing device domain. MFT, as advanced by Perlovsky, combines a priori knowledge representation with learning and fuzzy logic techniques to represent intellect. The mind operates through a combination of complicated a priori knowledge or experience with learning. The optimization of the CI sensor map strategy mimics this type of behavior since the tuning parameters may have different effects on different users.

Still, other computational methods can be used including, but not limited to, genetic algorithms, neural networks, fuzzy logic, and the like. Accordingly, the inventive arrangements disclosed herein are not limited to the use of a particular technique for formulating strategies for adjusting operational parameters of hearing devices based upon speech, or for determining relationships between operational parameters of hearing devices and recognition and/or perception of features of speech.

FIG. 3A is a table 300 listing examples of common operational parameters of hearing devices that can be modified through the use of a suitable control system, such as a computer or information processing system having appropriate software for programming such devices. FIG. 3B is a table 305 illustrating further operational parameters of hearing devices that can be modified using an appropriate control system. Accordingly, through an iterative testing process where a sampling of individuals are tested, relationships between test words, and therefore associated features of speech, and operational parameters of hearing devices can be established. By recognizing such relationships, strategies for improving the performance of a hearing device can be formulated based upon the CEM of a user undergoing testing. As such, hearing devices can be tuned based upon speech rather than tones.

Figure 4:
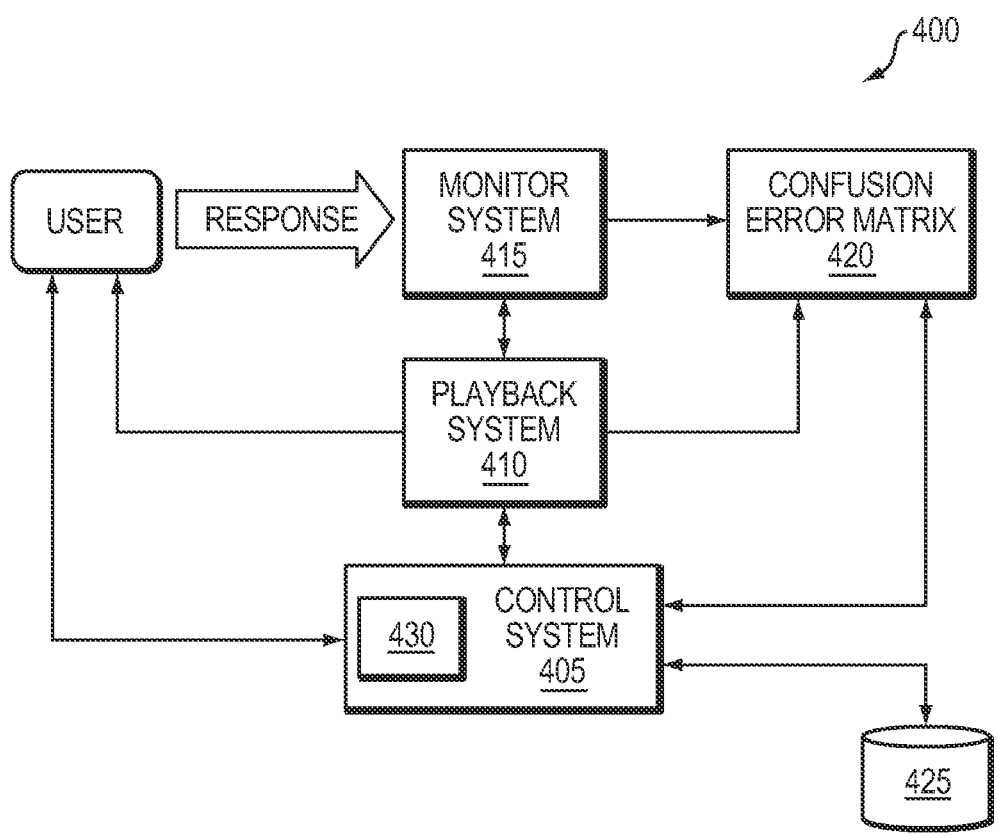
FIG. 4 is a schematic diagram illustrating an exemplary system for determining a mapping for a hearing enhancement system in accordance with the inventive arrangements disclosed herein.

FIG. 4 is a schematic diagram illustrating an exemplary system 400 for determining a mapping for a hearing device in accordance with the inventive arrangements disclosed herein. As shown, the system 400 can include a control system 405, a playback system 410, and a monitor system 415. The system 400 further can include a CEM 420 and a feature to map parameter knowledge base (knowledge base) 425.

The playback system 410 can be similar to the playback system as described with reference to FIG. 1. The playback system 410 can play audio renditions of test words and/or syllables and can be directly connected to the user's hearing device. Still, the playback system 410 can play words and/or syllables aloud without a direct connection to the hearing device.

The monitor system 415 also can be similar to the monitor system of FIG. 1. Notably, the playback system 410 and the monitor system 415 can be communicatively linked thereby facilitating operation in a coordinated and/or synchronized manner. For example, in one embodiment, the playback system 410 can present a next stimulus only after the response to the previous stimulus has been recorded. The monitor system 415 can include a visual interface allowing users to select visual responses corresponding to the played test audio, for example various correct and incorrect textual representations of the played test audio. The monitor system 415 also can be a speech recognition system or a human monitor.

The CEM 420 can store a listing of played audio along with user responses to each test word and/or syllable. The knowledge base 425 can include one or more strategies for improving the performance of a hearing device as determined through iteration of the method of FIG. 2. The knowledge base 425 can be cross-referenced with the CEM 420, allowing a mapping for the user's hearing device to be developed in accordance with the application of one or more strategies as determined from the CEM 420 during testing. The strategies can specify which operational parameters of the hearing device are to be modified based upon errors noted in the CEM 420 determined in the user's test session.

The control system 405 can be a computer and/or information processing system which can coordinate the operation of the components of system 400. The control system 405 can access the CEM 420 being developed in a test session to begin developing an optimized mapping for the hearing device under test. More particularly, based upon the user's responses to test audio, the control system 405 can determine proper parameter settings for the user's hearing device.

In addition to initiating and controlling the operation of each of the components in the system 400, the control system 405 further can be communicatively linked with the hearing device worn by the user. Accordingly, the control system 405 can provide an interface through which modifications to the user's hearing device can be implemented, either under the control of test personnel such as an audiologist, or automatically under programmatic control based upon the user's resulting CEM 420. For example, the mapping developed by the control system 405 can be loaded in to the hearing device under test.

While the system 400 can be implemented in any of a variety of different configurations, including the use of individual components for one or more of the control system 405, the playback system 410, the monitor system 415, the CEM 420, and/or the knowledge base 425, according to another embodiment of the present invention, the components can be included in one or more computer systems having appropriate operational software.

Figure 5:
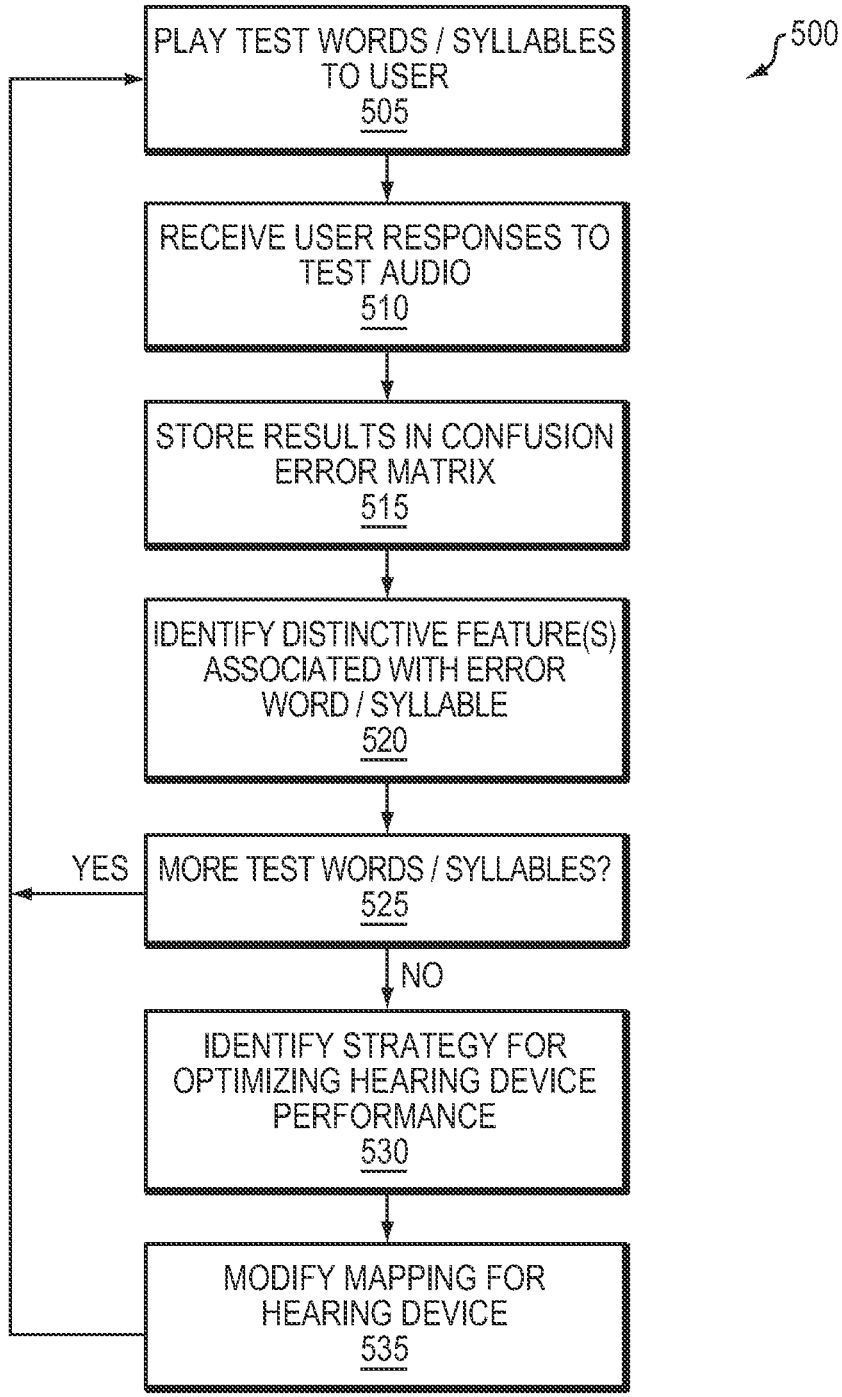
FIG. 5 is a flow chart illustrating a method of determining a mapping for a hearing enhancement system in accordance with the inventive arrangements disclosed herein.

FIG. 5 is a flow chart illustrating a method 500 of determining a mapping for a hearing device in accordance with the inventive arrangements disclosed herein. The method 500 can begin in a state where a user, wearing a hearing device, is undergoing testing to properly configure the hearing device. Accordingly, in step 505, the control system can instruct the playback system to begin playing test audio in a sequential manner.

As noted, the test audio can include, but is not limited to, words and/or syllables including nonsense words and/or syllables. Thus, a single word and/or syllable can be played. As portions of test audio are played, entries corresponding to the test audio can be made in the CEM indicating which word or syllable was played. Alternatively, if the ordering of words and/or syllables is predetermined, the CEM need not include a listing of the words and/or syllables used as the user's responses can be correlated with the predetermined listing of test audio.

In step 510, a user response can be received by the monitor system. The user response can indicate the user's perception of what was heard. If the monitor system is visual, as each word and/or syllable is played, possible solutions can be displayed upon a display screen. For example, if the playback system played the word "Sam", possible selections could include the correct choice "Sam" and an incorrect choice of "sham". The user chooses the selection corresponding to the user's understanding or ability to perceive the test audio.

In another embodiment, the user could be asked to repeat the test audio. In that case the monitor system can be implemented as a speech recognition system for recognizing the user's responses. Still, as noted, the monitor can be a human being annotating each user's response to the ordered set of test words and/or syllables. In any event, it should be appreciated that depending upon the particular configuration of the system used, a completely automated process is contemplated.

In step 515, the user's response can be stored in the CEM. The user's response can be matched to the test audio that was played to illicit the user response. It should be appreciated that, if so configured, the CEM can include text representations of test audio and user responses, recorded audio representations of test audio and user responses, or any combination thereof.

In step 520, the distinctive feature or features represented by the portion of test audio can be identified. For example, if the test word exhibits grave sound features, the word can be annotated as such. In step 525, a determination can be made as to whether additional test words and/or syllables remain to be played. If so, the method can loop back to step 505 to repeat as necessary. If not, the method can continue to step 530. It should be appreciated that samples can be collected and a batch type of analysis can be run at the completion of the testing rather than as the testing is performed.

In step 530, based upon the knowledge base, a strategy for adjusting the hearing device to improve the performance of the hearing device with respect to the distinctive feature(s) can be identified. As noted, the strategy can specify one or more operational parameters of the hearing device to be changed to correct for the perceived hearing deficiency. Notably, the implementation of strategies can be limited to only those cases where the user misrecognizes a test word or syllable.

For example, if test words having grave sound features were misrecognized, a strategy directed at correcting such misperceptions can be identified. As grave sound features are characterized by a predominance of energy in the low frequency range of speech, the strategy implemented can include adjusting parameters of the hearing device that affect the way in which low frequencies are processed. For instance, the strategy can specify that the mapping should be updated so that the gain of a channel responsible for low frequencies is increased. In another embodiment, the frequency ranges of each channel of the hearing device can be varied.

It should be appreciated that the various strategies can be formulated to interact with one another. That is, the strategies can be implemented based upon an entire history of recognized and misrecognized test audio rather than only a single test word or syllable. As the nature of a user's hearing is non-linear, the strategies further can be tailored to adjust more than a single parameter as well as offset the adjustment of one parameter with the adjusting (i.e. raising or lowering) of another. In step 535, a mapping being developed for the hearing device under test can be modified. In particular, a mapping, whether a new mapping or an existing mapping, for the hearing device can be updated according to the specified strategy.

It should be appreciated, however, that the method 500 can be repeated as necessary to further develop a mapping for the hearing device. According to one aspect of the present invention, particular test words and/or syllables can be replayed, rather than the entire test set, depending upon which strategies are initiated to further fine tune the mapping. Once the mapping is developed, the mapping can be loaded into the hearing device.

Different persons may form otherwise identical sounds and words differently, due to their particular speech models, which may include speech impediments, accents based on geographic origin, etc. In such a case, the person may be considered an "imperfect" transmitter (in that their speech is "impaired") and the ASR may be considered a "perfect" receiver. Accordingly, it is desirable to tune an ASR so any user's speech model may be effectively recognized by the ASR. Examples of systems and methods of tuning an ASR are described below with regard to FIGS. 6A-6C.

A proposed method for self-tuning an ASR system involves testing the user with a set of stimuli and generating a speech model for the user based on the difference between each stimulus and his corresponding response. This set of stimuli may be open or closed (i.e., limited to particular sounds that are particularly useful in perceptual testing). The difference between the stimulus and the response is analyzed in terms of certain features. The parameters of the ASR system are then tuned so that each time the recognized response is same as the stimulus.

Figure 6A:
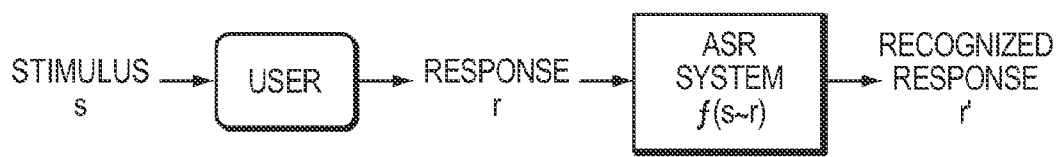
FIG. 6A is a flow chart illustrating a method of tuning an ASR system in accordance with the inventive arrangements disclosed herein.

One embodiment of the method associated with an ASR tuning system is depicted in FIG. 6A. There, if s is a stimulus to a user, r is his response, and r' is the recognized response from the ASR system, one goal of the tuning system is to minimize the difference between s and r'. This may be achieved by tuning the parameters of the ASR system, represented by the function $f$ of the difference between the stimulus s and the user's response r. The difference may be analyzed in terms of acoustic features, such as cepstral coefficients, speech features (such as grave, nasal, tense, strident, etc.), signal features (e.g., amplitude, phase, frequency, etc.), or a combination of the above. Additional features that may be analyzed are also contemplated and are described herein.

Figure 6B:
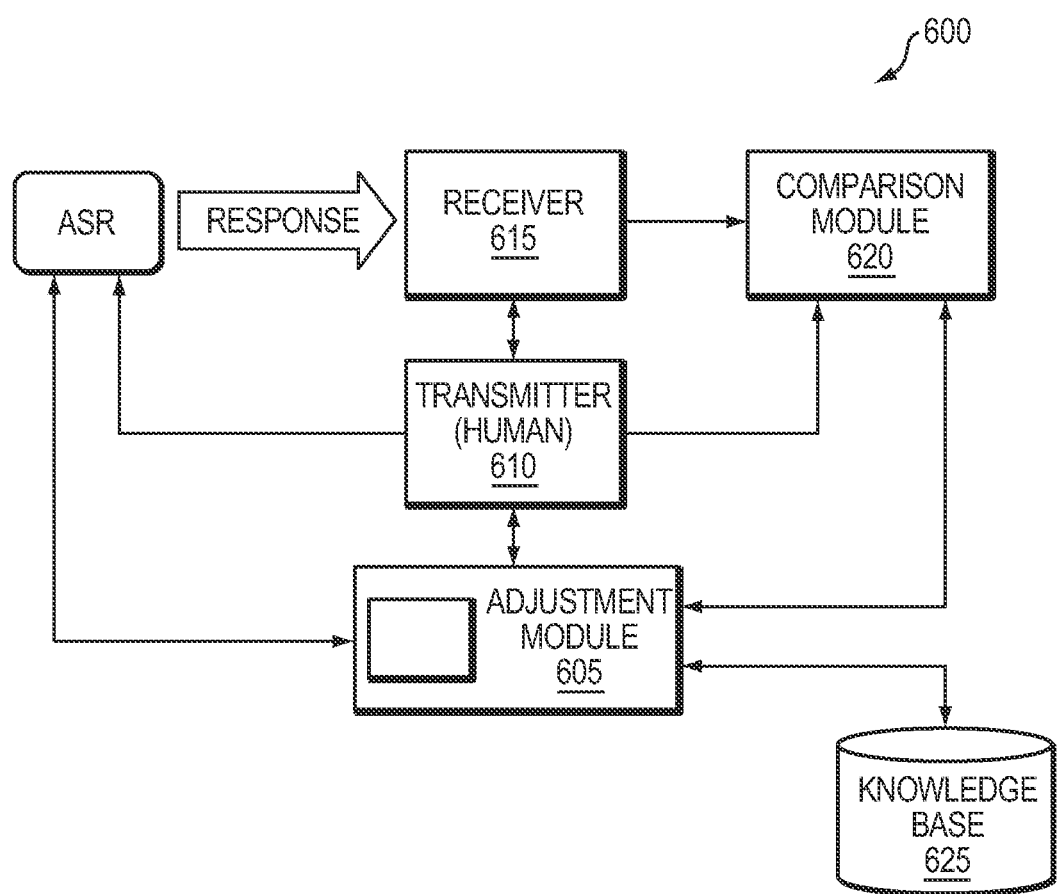
FIG. 6B is a schematic diagram illustrating an exemplary system for determining relationships between distinctive features of speech and adjustable parameters of an ASR system in accordance with the inventive arrangements disclosed herein.

FIG. 6B is a schematic diagram illustrating an exemplary system 600 for determining a mapping for an ASR system in accordance with the inventive arrangements disclosed herein. As shown, the system 600 can include an adjustment module 605, a transmitter 610, and a receiver 615. The system 600 further can include a comparison 620 and a feature to map parameter knowledge base (knowledge base) 625.

The transmitter 610 can be similar to the playback system described in FIG. 1. The transmitter 610 can play audio renditions of test words and/or syllables and can be directly connected to the ASR. Alternatively, in certain embodiments, the transmitter 610 may be a human user who is using the device into which the ASR is incorporated.

The receiver 615 can be similar to the monitor system described in FIG. 1. Notably, the transmitter 610 and the receiver 615 can be communicatively linked thereby facilitating operation in a coordinated and/or synchronized manner. For example, in one embodiment, the transmitter 610 can present a next stimulus only after the response to the previous stimulus has been recorded. The receiver 615, if implemented as the monitor system of FIG. 1, can include a visual interface allowing users to select visual responses corresponding to the played test audio, for example various correct and incorrect textual representations of the played test audio. In alternative embodiments, the receiver may send the recognized response r' to the comparison module 620.

The comparison module 620 may create a CEM similar to that described in FIG. 1, and can store a listing of played audio along with user responses to each test word and/or syllable. In alternative embodiments, the comparison module 620 may store any or all of the test stimulus s sent to the user, the user response r, and the ASR recognized response r'. The differences between the stimulus s, the user response r, and the ASR recognized response r' are determined by the comparison module 620, which creates a confusion error matrix. The confusion error matrix may be refer to, in one instance, the storage of errors between the stimulus and the response, as well as to the storage of errors using equations, logical expressions, stochastic/connectionist models, etc. In certain embodiments, the confusion error matrix compares the presented and produced phonemes. The matrix permits the calculation of measures that capture the accuracy of an ASR's recognized response with respect to the test stimuli. The data stored in the confusion error matrix might also be stored as: (1) algebraic functions (e.g., polynomials); (2) logical functions (e.g., first-order predicate logic); (3) one-dimensional arrays; (4) multi-dimensional matrices; (5) statistical models (e.g., Bayesian networks, Cox model, etc.); (6) connectionist models (e.g., parallel distributed processing networks, associative memory, etc.); or (7) rule-based models (e.g., if-then-else rules). Other modes of data storage are also contemplated. In general, the confusion error matrix encompasses all such functions/models that permit the calculation of measures to capture a patient's hearing ability.

The ASR may be tested with a closed set of simple nonsense sounds that are easy for the user to replicate in speech. Alternative testing may utilize actual words. One type of test may include presenting a set of stimuli to the user and recording his response corresponding to each stimulus, as well as the ASR recognized response. Assuming the user has normal hearing, the difference between the user response and the ASR recognized response represents the way the speaks and contributes to his speech model.

The speech model is unique to each user. One way to view the speech model is a set of points in high-dimensional space where each point represents the error at a particular ASR system parameter setting. The error is a function of the differences between each user response and the recognized response over an entire test. A tuning algorithm studies the speech model to predict the most plausible ASR parameters. With one or more tests, the optimal ASR system parameter settings can be reached so as to minimize the difference between s and r'.

Returning to FIG. 6B, knowledge base 625 can include one or more strategies for improving the performance of an ASR system as determined through iteration of the method of FIG. 5. The knowledge base 625 can be cross-referenced with the comparison module 620, allowing a mapping for the ASR system to be developed in accordance with the application of one or more strategies as determined from the comparison module 620 during testing. The strategies can specify which operational parameters of the ASR system are to be modified based upon errors noted in the confusion error matrix determined during a tuning session.

The control system or adjustment module 605 can be a computer and/or information processing system which can coordinate the operation of the components of the system 600, as well as adjust the operational parameters of the ASR system. The adjustment module 605 can access the comparison module 620 being developed in a test session to begin developing an optimized mapping for the ASR system being tuned. Based upon the user's responses to test stimuli, the adjustment module 605 can determine proper parameter settings for the ASR system.

In addition to initiating and controlling the operation of each of the components in the system 600, the adjustment module 605 further can be communicatively linked with the ASR system. Accordingly, the adjustment module 605 can provide an interface through which modifications to the user's hearing device can be implemented under programmatic control based upon the user's resulting confusion error matrix. For example, the mapping developed by the adjustment module 605 can be loaded in to the hearing device under test.

While the system 600 can be implemented in any of a variety of different configurations, including the use of individual components for one or more of the adjustment module 605, the transmitter 610, the receiver 615, the comparison module 620, and/or the knowledge base 625, according to another embodiment of the present invention, the components can be included in one or more computer systems having appropriate operational software. Alternatively, the system 600 may be incorporated directly into an ASR system that is used in a device.

Figure 6C:
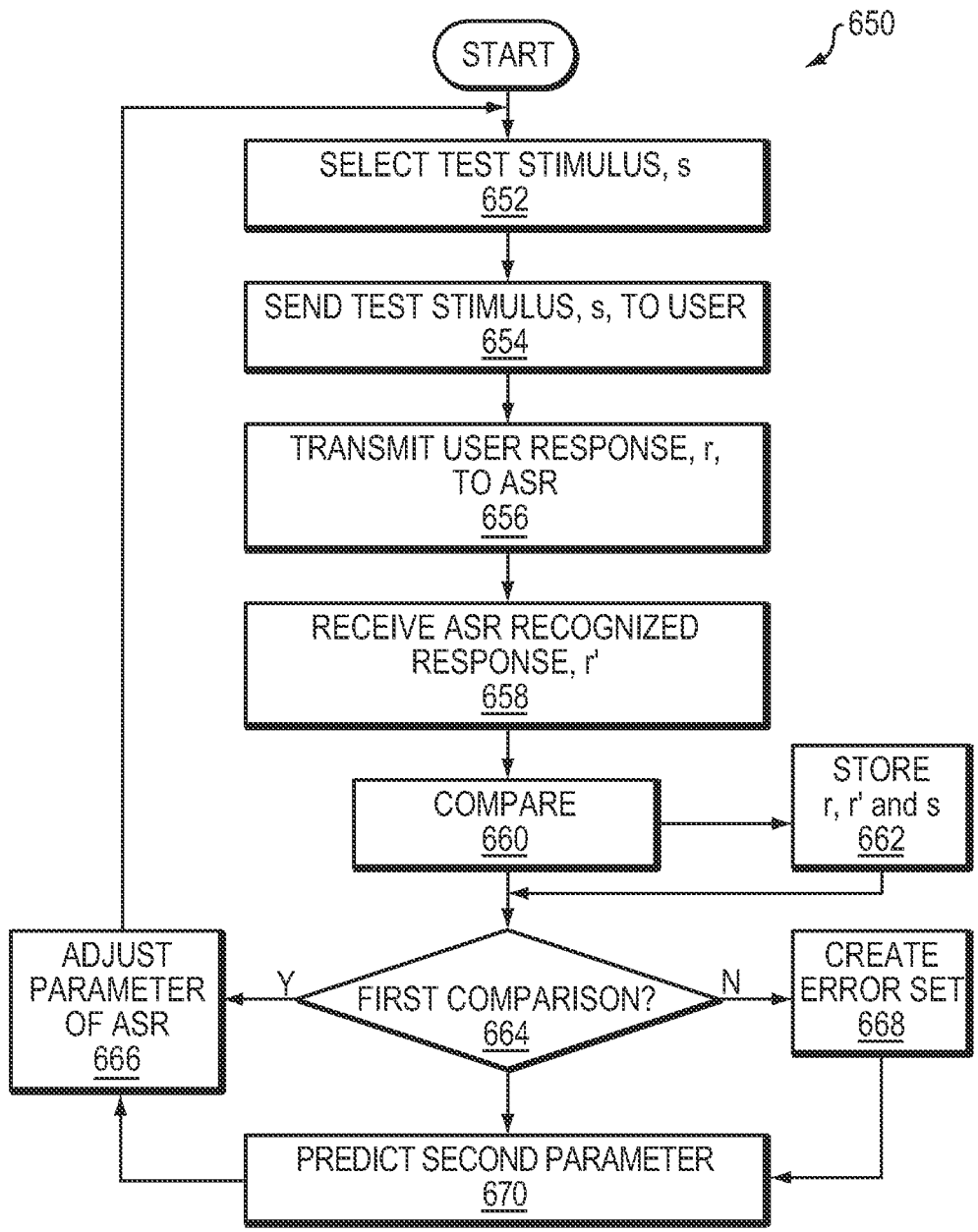
FIG. 6C is a schematic diagram of a method for tuning an ASR system in accordance with the inventive arrangements disclosed herein.

FIG. 6C depicts a method for tuning an ASR system in accordance with the inventive arrangements disclosed herein. The method may be performed by the tuning system depicted in FIG. 6B or by another embodiment of a tuning system. In the depicted method 650, a test stimulus s is first selected 652, in this case by an adjustment module that also acts as the primary control system for the tuning system. The adjustment module then sends the stimulus to a user 654. In the depicted embodiment, the adjustment module prompts the user to speak test stimulus, which may be a sound, phoneme, or word, as described above. The user then speaks the appropriate sound to the ASR, which is transmitted to the ASR as an associated user response r 656. This associated user response r is based on the test stimulus. Differences between the test stimulus s and the associated user response r may be due to the user speech model. The tuning system then receives the ASR recognized response r' from the ASR 658.

Next, the comparing step 660 compares two or more off the test stimulus s, the associated user response r, and the ASR recognized response r'. This comparison determines the differences between the two compared signals and creates the confusion error matrix. Thereafter, the signals may be stored 662 either in the confusion error matrix or in a separate storage module. If this is the first comparison 664 of a multi-comparison tuning session, the tuning system may adjust a parameter of the ASR system 666. If it is not the first comparison, the confusion error matrix may create an error set 668 based on any differences between any number of signals. As described above, as more differences are identified, the error set becomes more complex, leading to improved results of tuning the ASR system. Once an error set is created, the tuning system may predict additional parameters 670 based on known conditions, thus leading to increased tuning efficiency. Other tuning methods are also contemplated.

Those skilled in the art will recognize that the inventive arrangements disclosed herein can be applied to a variety of different languages. For example, to account for the importance of various distinctive features from language to language, each strategy can include one or more weighted parameters specifying the degree to which each hearing device parameter is to be modified for a particular language. The strategies of such a multi-lingual test system further can specify subsets of one or more hearing device parameters that may be adjusted for one language but not for another language. Accordingly, when a test system is started, the system can be configured to operate or conduct tests for an operator specified language. Thus, test audio also can be stored and played for any of a variety of different languages.

The present invention also can be used to overcome hearing device performance issues caused by the placement of the device within a user. For example, the placement of a cochlear implant within a user can vary from user to user. The tuning method described herein can improve performance caused, at least in part, by the particular placement of cochlear implant.

Still, the present invention can be used to adjust, optimize, compensate, or model communication channels, whether an entire communication system, particular equipment, etc. Thus, by determining which distinctive features of speech are misperceived or are difficult to identify after the test audio has been played through the channel, the communication channel can be modeled. The distinctive features of speech can be correlated to various parameters and/or settings of the communication channel for purposes of adjusting or tuning the channel for increased clarity.

For example, the present invention can be used to characterize the acoustic environment resulting from a structure such as a building or other architectural work. That is, the effects of the acoustic and/or physical environment in which the speaker and/or listener is located can be included as part of the communication system being modeled. In another example, the present invention can be used to characterize and/or compensate for an underwater acoustic environment. In yet another example, the present invention can be used to model and/or adjust a communication channel or system to accommodate for aviation effects such as effects on hearing resulting from increased G-forces, the wearing of a mask by a listener and/or speaker, or the Lombard effect. The present invention also can be used to characterize and compensate for changes in a user's hearing or speech as a result of stress, fatigue, or the user being engaged in deception.

The present invention can be realized in hardware, software, or a combination of hardware and software. The present invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The present invention also can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

In the embodiments described above, the software may be configured to run on any computer or workstation such as a PC or PC-compatible machine, an Apple Macintosh, a Sun workstation, etc. In general, any device can be used as long as it is able to perform all of the functions and capabilities described herein. The particular type of computer or workstation is not central to the invention, nor is the configuration, location, or design of a database, which may be flat-file, relational, or object-oriented, and may include one or more physical and/or logical components.

The servers may include a network interface continuously connected to the network, and thus support numerous geographically dispersed users and applications. In a typical implementation, the network interface and the other internal components of the servers intercommunicate over a main bi-directional bus. The main sequence of instructions effectuating the functions of the invention and facilitating interaction among clients, servers and a network, can reside on a mass-storage device (such as a hard disk or optical storage unit) as well as in a main system memory during operation. Execution of these instructions and effectuation of the functions of the invention is accomplished by a central-processing unit ("CPU").

A group of functional modules that control the operation of the CPU and effectuate the operations of the invention as described above can be located in system memory (on the server or on a separate machine, as desired). An operating system directs the execution of low-level, basic system functions such as memory allocation, file management, and operation of mass storage devices. At a higher level, a control block, implemented as a series of stored instructions, responds to client-originated access requests by retrieving the user-specific profile and applying the one or more rules as described above.

Communication may take place via any media such as standard telephone lines, LAN or WAN links (e.g., T1, T3, 56 kb, X.25), broadband connections (ISDN, Frame Relay, ATM), wireless links, and so on. Preferably, the network can carry TCP/IP protocol communications, and HTTP/HTTPS requests made by the client and the connection between the client and the server can be communicated over such TCP/IP networks. The type of network is not a limitation, however, and any suitable network may be used. Typical examples of networks that can serve as the communications network include a wireless or wired Ethernet-based intranet, a local or wide-area network (LAN or WAN), and/or the global communications network known as the Internet, which may accommodate many different communications media and protocols.

While there have been described herein what are to be considered exemplary and preferred embodiments of the present invention, other modifications of the invention will become apparent to those skilled in the art from the teachings herein. The particular methods of manufacture and geometries disclosed herein are exemplary in nature and are not to be considered limiting. It is therefore desired to be secured in the appended claims all such modifications as fall within the spirit and scope of the invention. Accordingly, what is desired to be secured by Letters Patent is the invention as defined and differentiated in the following claims, and all equivalents.

What is claimed is:

1. A non-transitory system memory encoding computer executable instructions that, when executed by at least one processor, perform a method comprising:
    sending an associated user response to the speech recognition system, wherein the associated user response is based at least in part on a test stimulus;
    receiving a recognized response from the speech recognition system, wherein the recognized response is based at least in part on the associated user response;
    comparing at least two of the test stimulus, associated user response, and the recognized response, and for generating a confusion error matrix, wherein the confusion error matrix comprises test stimulus and the recognized response; and
    adjusting at least one parameter of the speech recognition system based at least in part on the confusion error matrix.

2. The system memory of claim 1, wherein the method further comprises sending a test stimulus to a user.

3. The system memory of claim 1, wherein the method further comprises:
    comparing the associated user response to the recognized response;
    identifying an error between the associated user response to the recognized response; and
    storing the error in the confusion error matrix.

4. The system memory of claim 3, wherein the method further comprises comparing an acoustic feature of the test stimulus to an acoustic feature of the associated user response.

5. The system memory of claim 4, wherein the acoustic feature comprises at least one of a cepstral coefficient and a speech feature.

6. The system memory of claim 3, wherein the method further comprises adjusting the at least one parameter based at least in part on the error.

7. The system memory of claim 6, wherein the method further comprises predicting at least a second parameter based at least in part on the error.

8. The system memory of claim 3, wherein the method further comprises storing at least one of the test stimulus, the associated user response, and the recognized response.

9. The system memory of claim 3, wherein the method further comprises storing a plurality of test stimuli, a plurality of associated user responses, and a plurality of recognized responses.

10. The system memory of claim 9, wherein the method further comprises comparing at least two of the plurality of test stimuli, the plurality of associated user responses, and the plurality of recognized responses and generates a speech model based at least on part on the comparison.

11. The system memory of claim 1, wherein the method further comprises:
    comparing the test stimulus to the recognized response;
    identifying an error between the test stimulus to the recognized response; and
    storing the error in the confusion error matrix.

12. A method of tuning a speech recognition system, the method comprising:
   transmitting an associated user response to a speech recognition system, wherein the associated user response is based at least in part on a test stimulus;
   receiving a recognized response from a speech recognition system, wherein the recognized response is based at least in part on the associated user response;
   comparing at least two of the test stimulus, associated user response, and the recognized response;
   generating a confusion error matrix, wherein the confusion error matrix comprises test stimulus and the recognized response; and
   adjusting at least one parameter of a speech recognition system based at least in part the confusion error matrix.

13. The method of claim 12, further comprising:
   selecting a test stimulus; and
   sending the test stimulus to a user.

14. The method of claim 13, wherein the comparing operation comprises comparing the associated user response to the recognized response.

15. The method of claim 14, further comprising storing the associated user response.

16. The method of claim 14, wherein comparing at least two of the test stimulus, associated user response, and the recognized response comprises comparing an acoustic feature of the associated user response to an acoustic feature of the recognized response.

17. The method of claim 16, wherein the acoustic feature comprises at least one of a cepstral coefficient and a speech feature.

18. The method of claim 12, wherein the confusion error matrix comprises a first difference between a first associated user response and a second recognized response and a second difference between a second associated user response and a second recognized response.

19. The method of claim 18, further comprising predicting at least a second parameter based at least in part on the confusion error matrix.

20. A system comprising:
   at least one processor; and
   memory encoding computer executable instructions that, when executed by the at least one processor, perform a method comprising:
      transmitting an associated user response to a speech recognition system, wherein the associated user response is based at least in part on a test stimulus;
      receiving a recognized response from a speech recognition system, wherein the recognized response is based at least in part on the associated user response;
      comparing at least two of the test stimulus, associated user response, and the recognized response;
      generating a confusion error matrix, wherein the confusion error matrix comprises at least one error between the test stimulus and at least one of the user response and the recognized response; and
      adjusting at least one parameter of a speech recognition system based at least in part the confusion error matrix.

21. The system of claim 20, wherein the confusion error matrix comprises a first difference between a first associated user response and a second recognized response and a second difference between a second associated user response and a second recognized response.

* * * * *